United States Patent [19]

Lipinski

[11] Patent Number: 5,607,841
[45] Date of Patent: Mar. 4, 1997

[54] PREPARATION AND PROTEOLYTIC DEGRADATION OF A MACROMOLECULAR PROTEIN COMPLEX FROM FIBRINOGEN

[76] Inventor: Boguslaw Lipinski, 97 Beaumont Ave., Newtonville, Mass. 02160

[21] Appl. No.: 262,607

[22] Filed: Jun. 20, 1994

[51] Int. Cl.$^6$ .............................. C12P 21/06; C07K 1/12; C07K 14/745
[52] U.S. Cl. .......................... 435/68.1; 530/350; 530/417
[58] Field of Search ..................................... 530/389, 350; 435/68.1

[56] References Cited

U.S. PATENT DOCUMENTS

| | | | |
|---|---|---|---|
| 3,895,107 | 7/1975 | Morrison | 514/54 |
| 4,381,346 | 4/1983 | Hussin et al. | 435/215 |
| 4,602,005 | 7/1986 | Malinow | 514/26 |
| 4,673,573 | 6/1987 | Ferres et al. | 424/94.63 |
| 5,004,802 | 4/1991 | Kluft | 530/380 |
| 5,011,686 | 4/1991 | Pang | 424/94.1 |
| 5,089,602 | 2/1992 | Isliker et al. | 530/359 |
| 5,096,696 | 3/1992 | Galanakis | 424/1.69 |
| 5,116,613 | 5/1992 | Haber et al. | 424/178.1 |
| 5,261,255 | 11/1993 | Coelho et al. | 62/376 |
| 5,290,915 | 3/1994 | Nakao et al. | 530/350 |

OTHER PUBLICATIONS

Brewer et al. (1974) "Experimental Techniques in Biochemistry", Prentice–Hall, Inc., Englewood Cliffs, pp. 325–328.
Sigma (1992) "Biochemicals and Organic Compounds" (Catalog), p. 1574.
Sobel et al., "Monoclonal Antibody to the Region of Fibronectin Involved in Cross–linking to Human Fibrin", Biochemistry, vol. 22, pp. 4175–4183 (1983).

Bisbee, C. A., "Development of Thrombolytic Therapeutics and Lessons Learned from tPA", Genetic Engineering News, Dec. 1993, p. 10.

Phaneuf et al., "Covalent Linkage of Streptokinase to Recombinant Hirudin: A novel thrombolytic Agent with Antithrombotic Properties", Thrombos. Haemost. vol. 71, pp. 481–487 (1994).

Shohet et al., "Inhibitor–resistant Tissue–type Plasminogen Activator: An Improved Thrombolytic Agent *In Vitro*", Thrombos. Haemost. vol. 71, pp. 124–128 (1994).

Takada et al., "Effects of Heparin Sulfate Analogue or Other Sulfated Polysaccharides on the Activation of Plasminogen by t–PA or u–PA", Thrombos. Res. vol. 73, pp. 301–311 (1994).

*Primary Examiner*—Michael G. Wityshyn
*Assistant Examiner*—Jon P. Weber

[57] ABSTRACT

A method for preparing a macromolecular protein complex (MPC) from fibrinogen in human plasma by the steps of ammonium sulfate precipitation, dialysis and gel filtration is disclosed. The isolated MPC may be degraded by contacting with trypsin. The isolated MPC inhibited fibrinolysis induced with plasminogen but not with plasmin. Elimination of the MPC by means of chondroitin sulfate A restored normal fibrinolysis. An antibody to fibrin-binding peptides which are produced by trypsin degradation of MPC, was conjugated to plasmin. The anti-MPC peptide antibody/plasmin conjugate has the capacity to bind to MPC-rich thrombus and degrade it without activation of fibrin-bound plasminogen.

4 Claims, 2 Drawing Sheets

PREPARATION AND PROTEOLYTIC DEGRADATION OF A MACROMOLECULAR PROTEIN COMPLEX FROM FIBRINOGEN

BACKROUND OF THE INVENTION

Fibrin and fibrin-like deposits in human organs have been observed in diseases including atherosclerosis, viral and bacterial infections, cancer and diabetic nephropathy. Similar deposits were also observed in endotoxin-induced thrombosis in rabbits. In both human diseases as well as in experimental thrombosis the concentration of fibrinogen in blood is significantly increased. It was therefore concluded that elevated plasma fibrinogen is an important factor contributing to thrombosis and atherosclerosis (Ernst, E. *Annals of Medicine* 26, 15–22, 1994). There is, however, no explanation why an approximately one ml thrombus containing 3–6 mg of fibrin should be formed preferentially in blood with a high fibrinogen level (6,000 mg/l) rather than in blood with a normal level (3,000 mg/l). In both cases there is a thousand-fold excess of circulating fibrinogen over that utilized to to form fibrin in the thrombus. These observations suggest that there must be some other factor(s) which contribute to the formation and persistence of fibrin in pathologic states.

The discovery by the present inventor of a macromolecular protein complex (MPC) in human plasma offers an explanation for this puzzle. It should be emphasized that MPC is a very elusive protein and thus difficult to identify. It is, for example, not present in serum since it is removed with fibrin during blood coagulation. During electrophoresis using polyacrylamide gel, agarose gel or other supporting media, MPC remains immobile at the application point and thus cannot be compared to any known protein. Another reason for the failure of MPC detection by other researchers is that during purification of human fibrinogen by fractional precipitation of plasma, with ammonium sulfate, ethanol or ethyl ether, a part of a cold-insoluble precipitate is routinely discarded as a denatured protein. When such coid-precipitable fraction of human plasma was subjected to exclusion chromatography, two protein peaks were obtained. The first peak contained a thrombin-unclottable protein eluted with void volume of the column followed by a second peak of fibrinogen.

The discovery of MPC is of a great significance leading to the development of novel thrombolytic therapies in accordance with the present invention. Current therapies with fibrin specific tissue plasminogen activator (t-PA) or non-specific urokinase (u-PA) and streptokinase (SK) require unproportionately large doses of these agents. It is paradoxical that in order to degrade a thrombus, usually containing no more than 10 mg of fibrin and a fraction of a mg of a fibrin-bound plasminogen, such huge quantities of activators have to be infused (e.g. 100 mg of t-PA). The relative lack of superiority of one thrombolytic agent over another, despite their claimed increased fibrin specificity was recently emphasized by Stoughton et al. in *Journal of Vascular Surgery,* 19, 298–305, 1994. Virtually each instance of thrombolytic therapy which results in effective dissolution of the thrombus is followed by some degree of plasminemia. These phenomena can now be explained in terms of the masking effect of MPC on fibrin-bound plasminogen. Because this masking is so complete, no excess of activator can penetrate the protective coat of MPC until it is degraded by active plasmin formed from plasminogen circulating in the blood.

Thus, an object of this invention is the preparation of an antibody to a specific fragment of the MPC-fibrin complex, which antibody is coupled to active plasmin and a proteolytic enzyme capable of degrading MPC-fibrin without the involvement of plasminogen in the complex. The need for new thrombolytics was recently discussed in an article entitled "Development of Thrombolytic Therapeutics" on page 10 of the *Genetic Engineering News*, December, 1993. The plasminogen-independent enzymic thrombolytic agent (PIETA) prepared according to the present invention inexpensively achieves rapid and complete thrombolysis. At the present time the cost of thrombolytic therapies in the US alone is over $300 million. This invention, therefore, should lead to a dramatic decrease of the cost of thrombolytic therapy due to the fact that much lower amounts of agents are needed to achieve effective thrombus dissolution in viva.

SUMMARY OF THE INVENTION

This invention is based on a discovery by the present inventor of a new macromolecular protein complex (MPC) in blood of patients with cardiovascular disease. This protein, although it exists in plasma at a relatively low concentration, dramatically affects the properties of the fibrin clot. MPC is not related to fibrinogen and therefore is not clottable with thrombin, but it becomes incorporated into fibrin thus significantly increasing its mass and resistance to lysis. MPC being tightly bound to the fibrin mesh through hydrophobic interactions, makes plasminogen in the clot unavailable for activation with u-PA, t-PA, or SK. The present invention offers an explanation for a number of problems associated with current thrombolytic therapies. Progressive resistance of coronary thrombi to lysis within hours of onset of myocardial infarction is likely to be caused by the accumulation of circulating MPC in the clot. This not only increases the mass of thrombi, but also prevents plasminogen from being activated by injected thrombolytics even at a large excess with respect to thrombus size. The same fact explains why fibrin-specific activators, such as t-PA, fail to induce thrombolysis at the desired low doses. Succesful thrombolytic therapy is, as a rule, associated with some degree of plasminemia. Thus, only when active plasmin is being generated, effective thrombolysis can take place bypassing plasminogen activation within the thrombus. However, this is an undesirable mechanism which may lead to internal bleeding and even death of the patient.

To overcome these problems a novel plasminogen-independent enzymic thrombolytic agent (PIETA) has been designed which possesses the following characteristics: 1. binds to MPC-fibrin complex, 2. degrades this complex without activation of plasminogen in the thrombus, 3. does not induce systemic plasminemia and fibrinogenolysis. PIETA is made of two components joined by means of a chemical bond, namely anti-MPC-fibrin antibody and an active proteolytic enzyme. To prevent self-proteolysis, one embodiment of PIETA is designed to have a proenzyme (e.g. chymotrypsinogen) in its molecule which is then activated with trypsin just prior to use. Where an active enzyme is conjugated to the antibody, self-digestion is inhibited with alpha-2-antitrypsin which is added to the preparation. The mechanism of action of PIETA is based on its specific binding to MPC-fibrin complex and its solid phase digestion by the proteolytic enzyme of the PIETA conjugate in this way even old thrombi can be successfully degraded with only a small amount of this novel thrombolytic agent without inducing generalized plasminemia and fibrinogenolysis, both of which are known to contribute to the complications arising out of current thrombolytic therapies.

DETAILED DESCRIPTION OF THE INVENTION

Figure 1:
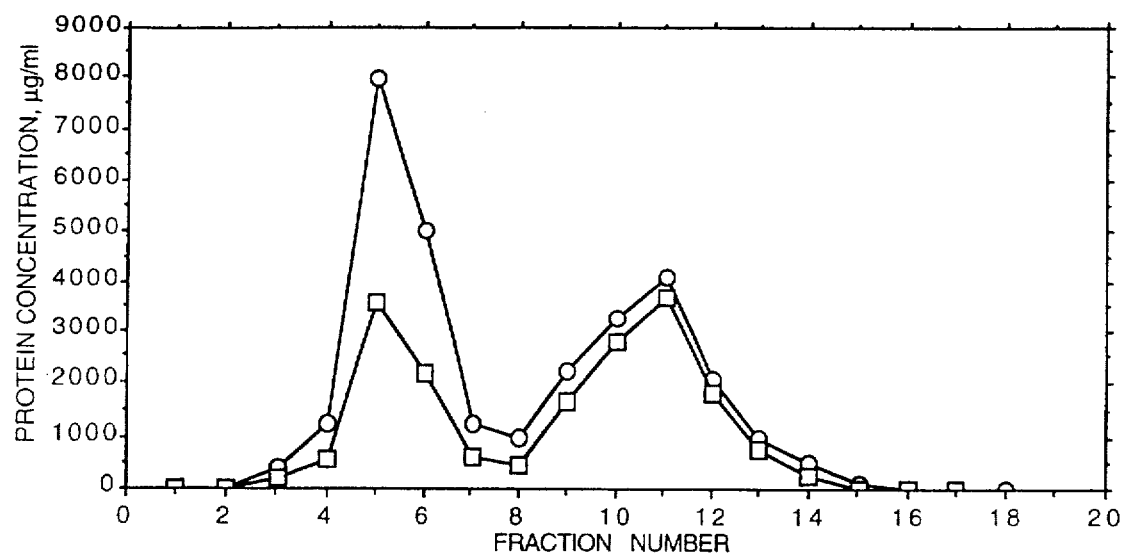
FIG. 1. Elution profile from Sepharose 6B of a cold-insoluble precipitate obtained from human plasma. Fractions No. 4–6, eluted with a void volume of the column contained an opalescent protein complex which was unclottable with thrombin. Fractions 9–13 contained fibrinogen (protein clottable with thrombin).

The macromolecular protein complex (MPC) is isolated from a single donor or pooled plasma of CVD patients, by means of precipitation with ammonium sulfate (20–40% saturation), dialysis in cold against an appropriate buffer, and finally by exclusion chromatography (see FIG. 1). The final step allows for separation of MPC from a thrombin clottable protein i.e. fibrinogen. The molecular weight of MPC is in the range of 1,000 kDa-5,000 kDa and that of fibrinogen is 340 kDa. Mixing MPC with fibrinogen obtained from the same chromatographic run of the cold-insoluble fraction and clotting the mixture with thrombin increased the amount of protein in fibrin clots up to 200%. This can be explained in terms of the interaction between the hydrophobic groups of disulfide crosslinked polypeptide chains of MPC and the apolar regions of fibrin which become exposed during its conversion from fibrinogen catalysed by thrombin (van Oss, C. J. *Journal Protein Chemistry* 9,487–491,1990). The incorporation of MPC to fibrin, however, can be prevented by certain glycosaminoglycans, for example chondroitin sulfate A (CSA), chondroitin sulfate C, dermatan sulfate, keratan sulfate and carboxymethylated sulfo-chitosan. This particular property of CSA was then utilized to demonstrate the existence of MPC in patients plasma (Table 1).

TABLE 1

Mean values ± SD for fibrinogen determined as a fibrin clot (Fibrin) formed in the presence and absence of chondroitin sulfate A (CSA) at the concentration of 2 mg/ml, in plasma of 10 cardiovascular patients.

| Fibrin-Saline | Fibrin-CSA | Difference | |
|---|---|---|---|
| mg/dl | mg/dl | mg/dl | percent |
| 481 ± 158 | 280 ± 108 | 201 ± 75 | 42 ± 16 |

Chondroitin sulfate prevents MPC from binding to fibrin most likely by blocking the hydrophobic interaction between these two proteins. This finding may explain why the administration of this class of substances to diabetic patients caused a decrease in their plasma fibrinogen levels (Ceriello, A. et al. *Diabetes Nutrition Metabolism*, 6,203–206, 1993).

An even more important property of the macromolecular protein complex was discovered by the present inventor with respect to fibrinolysis. As shown previously by the inventor and his coleagues, intravascular fibrin degradation is induced by binding a specific blood plasminogen activator (scu-PA) to fibrin (see U.S. Pat. No. 4,381,346). The present invention is based on a new observation that, by contrast to normal plasma, washed fibrin clots obtained from the plasma of patients with cardiovascular disease (CVD)were completely resistant to fibrinolysis induced with a large excess of urokinase (u-PA), sterptokinase (SK) and tissue plasminogen activator (t-PA) alike. However, the addition of human plasminogen to the incubating media resulted in prompt dissolution of the clots (Table 2 below).

TABLE 2

Lysis time of washed fibrin clots obtained from plasma of CVD patients with and without human plasminogen added to the incubating media containing various plasminogen activators.

| Incubating medium | u-PA | SK | t-PA |
|---|---|---|---|
| Saline | no lysis over 18 hours | | |
| Plasminogen | 60 min. | 85 min. | 180 min. |

Figure 2:
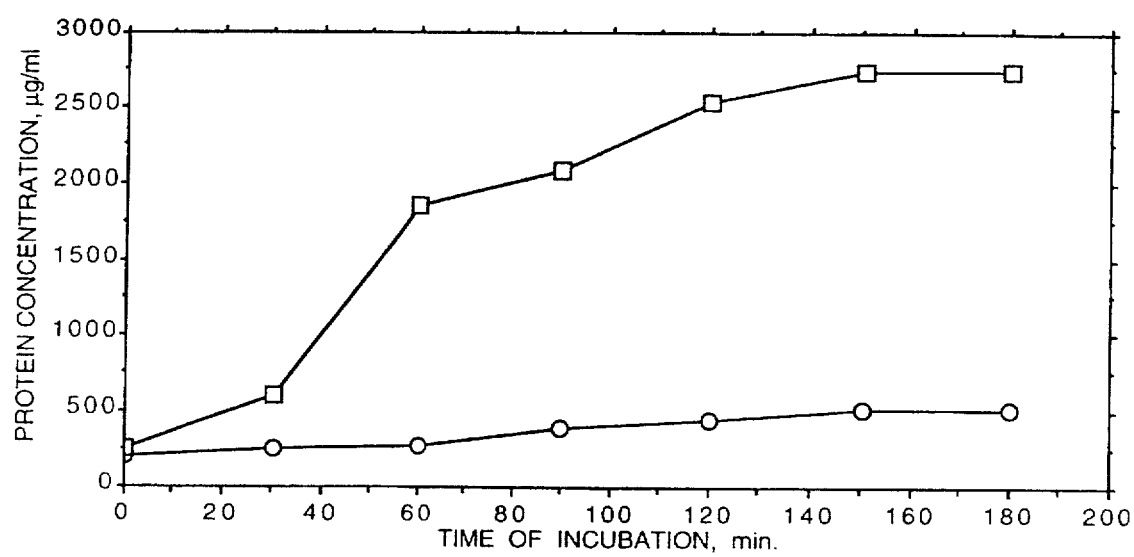
FIG. 2. Release of protein into solution from washed fibrin clots prepared with (□) and without (O) CSA under the influence of u-PA during the incubation at 37° C.

These results point to the conclusion that plasminogen molecules bound to fibrin are covered up by MPC and thus cannot be activated by the external activators. By contrast, the same clots can be dissolved by active plasmin formed from the plasminogen added to the incubating medium. Apparently, the macromolecular protein complex covering the plasminogen and fibrin is being enzymatically degraded by the action of plasmin formed from externally added plasminogen. The involvement of MPC in the inhibition of activation of plasminogen bound to fibrin is also demonstrated by the effect of CSA on urokinase-induced fibrinolysis (see FIG. 2). The addition of a solution of CSA to a patient's plasma prior to the preparation of the washed fibrin clot resulted in complete fibrinolysis during incubation with the urokinase-type plasminogen activator alone. By contrast, the clot formed without CSA was completely resistant to lysis.

The above described experiments clearly indicate that MPC has a very significant effect on fibrinolysis. The putative mechanism of this inhibition is that MPC is blocking plasminogen molecules bound to fibrin thus preventing them from being activated by the plasminogen activators. Such a complex of fibrin with MPC is not, however, resistant to plasmin degradation, since addition of external plasminogen restores normal fibrinolysis.

The preparation of a novel thrombolytic agent in accordance with the present invention is described in the following manner. First, a purified preparation of MPC is digested with various proteases e.g. trypsin, chymotrypsin, papain or pepsin. The peptides formed as a result of the digestion are then separated by affinity chromatography using fibrin/Celite. The purpose of this step is to isolate those fragments of MPC which are responsible for binding to fibrin. The digestion mixture is passed through a column filled with fibrin/Celite followed by extensive washing to remove any unbound material. The peptides with fibrin affinity are them eluted with a buffer containing sodium dodecyl sulfate (SDS) and are further purified using Sephadex G-25 and G-50 columns. After freeze-drying the peptides are conjugated to keyhole-limpet hemocyanin (KLH) and used for immunization of rabbits to produce antibodies to fibrin-binding fragments of MPC. The antibody titer is determined by means of ELISA method using MPC-derived peptides conjugated to bovine serum albumin (BSA) as an antigen, and goat anti-rabbit IgG-alkaline phosphatase as a secondary antibody. Antibody-containing immunoglobulins are purified by means of chromatography with Agarose-Protein A column. The immunoglobulin Fab' fragment is prepared by digestion with pepsin.

An embodiment of the present invention is described as follows. The Fab' fragment of the anti-MPC/fibrin antibody is chemically conjugated by bifunctional crosslinking reagents to active plasmin or other proteolytic enzymes, such as chymotrypsin, papain, bromelain and cathepsins. In order to prevent self-digestion of such a conjugate, a small amount of human alpha-2-antitrypsin (final concentration of 1-50 nM) is added to each preparation. The inhibitory effect of this protein is then eliminated in the presence of fibrin which causes its dissociation with a liberation of active antibody-enzyme conjugate capable of degrading fibrin clots. In another embodiment a thrombolytic agent is prepared by coupling anti-MPC-fibrin antibody to a proenzyme e.g. chymotrypsinogen. The conjugate is then activated by addition of small amount of trypsin or any other suitable activator prior to intravenous injection. After a short period of time trypsin activates chymotrypsinogen to chymotrypsin, and free trypsin is inactivated by circulating plasma inhibitors. Although chymotrypsin in the conjugate is also inactivated by the same inhibitors, after it is bound to the fibrin clot the inhibitors are dissociated and chymotrypsin is free to digest a solid phase fibrin-MPC complex. This mechanism is no different from that operating when plasminogen activators circulating in blood activate only those molecules of plasminogen which are bound to fibrin. Effective clot lysis is possible because fibrin-bound plasmin is not inactivated by circulating inhibitors e.g. alpha-2-antitrypsin or antiplasmin.

The most significant advantage of this novel thromoblytic agent is that, due to its specific degradation of MPC in the fibrin clot, it can lyse old thrombi. It is well known that the present thrombolytic agents can achieve dissolution of thrombi which are relatively fresh: 3–6 hours after the onset of infarct. According to the present invention, this is due to a gradual build up of MPC on the surface of fibrin in the thrombus, making it completely unaccessible to the infused plasminogen activators. Effective thrombolysis can only occur after the activators convert some of the circulating plasminogen to plasmin which then degrade both MPC and fibrin in the thrombus. The novel thrombolytic agent overcomes this problem due to its ability to bind and degrade the macromolecular protein complex in thrombi irrespectively of their age i.e amount of MPC bound to fibrin. Additional applications of this plasminogen-independent thrombolytic agent are in therapy of pulmonary embolism, deep vein thrombosis and acute ischemic stroke which together account for a half million hospitalizations in the U.S. each year.

EXAMPLES

The following examples serve to provide further appreciation of the invention but are not meant in any way to restrict the effective scope of the claims.

EXAMPLE 1

Isolation of a Macromolecular Protein Complex and Preparation of Antigens

The macromolecular protein complex was isolated from human plasma by the following method. Ten ml of saturated ammonium sulfate was added with mixing to 20 ml of human plasma and left at room temp. for 15 min. After centrifugation at 2,000 xg for 10 min the precipitate was washed with 2×20 ml of 30% ammonium sulfate, dissolved in 3 ml of Tris buffer pH 7.4 and dialysed against cold distilled water for 18 hrs. The precipitate formed during dialysis was dissolved in 2 ml of Tris buffer pH 7.4 containing 0.02% sodium azide and 1 mM EDTA, and then applied to Sepharose 6B column (15×300 mm) equilibrated with the same buffer. Two ml fractions were collected at a rate of one ml/8 min and the protein content was determined spectrophotometrically at 280 nm using a standard curve prepared with pure human serum albumin.

Peptide fragments of MPC with fibrin affinity were prepared as follows. Two hundred mg purified MPC was dissolved in 5 ml with Tris-NaCl-10 mM $CaCl_2$ buffer pH 7.4 and digested with trypsin (100 µg/ml) for 18 hrs at 37° C. Peptides obtained by proteolytic degradation of MPC were then chromatographed on fibrin/Celite (Husain, S. S. et al. *Archives Biochemistry Biophysics*, 220,31–38, 1983). Hyflo Super-Cel (Celite, 20 g) was washed to remove fine particles and further washed on a Buchner funnel with 0.05 M phosphate buffer, pH 7.4, containing 0.1M NaCl and 1 mM EDTA (buffer A). The washed Celite was suspended in 50 ml buffer A and mixed with 50 ml of 2% fibrinogen solution followed by addition of 200 units of bovine thrombin with constant stirring. After 15 min the suspension was filtered and washed with buffer A and packed into a column (0.7×10 cm) using the same buffer. The column was then equilibrated with buffer A containing 5 mM epsilon-aminocaproic acid to prevent fibrinolytic degradation.

Five ml portions of MPC trypsin digest was passed through the column and eluted with buffer A containing increasing quantities of NaCl (0–1M), then again with buffer A containing SDS (0–2%). The peptides eluted were concentrated in vacuum and further purified by gel filtration using a column with Sephadex G-50 equilibrated with 0.05 sodium acetate buffer, pH 4.6. Those MPC fragments which showed the highest affinity to fibrin were conjugated to KLH and used as antigens for immunization of rabbits.

EXAMPLE 2

Preparation of Anti-MPC Antibody and Conjugation with Plasmin

MPC-derived peptides, prepared as described in Example 1, were used to immunize rabbits in the following way. First, rabbits were injected with each peptide containing 250 µg of the material in 250µl of a Complete Freund Adjuvant, followed by 5 weekly injections of 100 µg in 100 µl of Incomplete Adjuvant. Blood samples were drawn before (preimmunization) and then 3 and 6 weeks of the immunization to test for the antibody titer by means of ELISA method. Purified MPC-derived peptides were used as antigens and goat-anti-rabbit Ig G conjugated with alkaline phophatase as a secondary antibody. The highest titer (1:248 000) was obtained with peptide No. 4 eluted from fibrin/Celite with buffer A and 2% SDS. Ig G from serum HS-4 was isolated utilizing an agarose- -protein A column, and the purified immunoglobulin Fab' fragment conjugated to human plasmin by the following method. First, maleimide groups were introduced into plasmin by reacting 4 mg of this protein with 1 mg of N-succinimidyl 4(N-maleidomethyl) cyclohexane-1-carboxylate (Pierce Chem. Co.) for one hour at 30° C. with continuous shaking. The mixture was then separated on Sephadex G-25 column (10×400 mm) equilibrated with Tris buffer pH 7.0. Fractions containing maleimide-plasmin were mixed with 100 nmol of Fab' fragment of HS-4 antibody obtained by pepsin digestion of a corresponding IgG, and kept at 4° C. for 20 hrs. After blocking the remaining maleimide groups with 2-mercaptoethylamine, the mixture was separated on Sephadex G-200 column (15×450 mm) equilibarted with Tris buffer pH 7.4 containing 0.02% NAN,. Three ml fractions were collected and those containing the antibody-plasmin conjugate were stored at 4° C.

EXAMPLE 3

Non-enzymatic Enhancement of Fibrinolysis with Chondroitin Sulfate A

Two hundred fifty μl portions of EDTA plasma obtained from a patient with CVD were mixed with 100 μl of water and 100 μl of chondroitin sulfate A (CSA) (Sigma Chem. Co.) respectively, and with 500 μl of Tris-NaCl buffer pH 7.4 containing 10 mM $CaCl_2$. The two mixtures were clotted with 10 μl of thrombin (50–100 U/ml) and incubated at 37° C. for 30 min. The fibrin clots were allowed to soak on a stack of filter papers, washed in Tris buffer without calcium, blotted between filter papers and placed in polypropylene test tubes. The clots were then incubated with 100 units of urokinase (Abbott Labs.) in Tris buffer pH 7.4 and the time of complete dissolution of the clots observed. Only fibrin clots prepared in the presence of CSA dissolved within 2–3 hours of incubation at 3° C. The control clots prepared in the presence of water did not lyse in over 18 hours of incubation.

The foregoing decription is offered by way of illustration and in fulfillment of the applicant's duty to disclose the best mode for the practice of the invention. Accordingly, the above procedures may be modified within the skill of the art and all such modifications are contemplated herein and made a part of hereof.

I claim:

1. A method for isolating a macromolecular protein complex from fibrinogen present in human plasma comprising the steps of:
   (a) precipitating protein from human plasma by adding one volume of saturated aqueous ammonium sulfate to two volumes of plasma;
   (b) washing the precipitate with aqueous ammonium sulfate;
   (c) dissolving the precipitate in a buffer and dialyzing it against distilled water;
   (d) chromatographing the dissolved dialyzed precipitate obtained in step (c) by gel filtration to separate said macromolecular protein complex.

2. The method of claim 1 wherein the precipitate in step (b) is washed with 30 percent aqueous ammonium sulfate.

3. The method of claim 1 wherein the precipitate in step (c) is dialyzed against cold distilled water.

4. A method for proteolytic degradation of the macromolecular protein complex obtained according to claim 1 by contacting said macromolecular protein complex with trypsin.

* * * * *